United States Patent [19]
Harrison et al.

[11] Patent Number: 5,922,744
[45] Date of Patent: Jul. 13, 1999

[54] ETHANE-1-2-DIAMINE DERIVATIVES AND TACHYKININ ANTAGONISTS

[75] Inventors: Timothy Harrison, Great Dunmow; Andrew Pate Owens, Ellington Thorpe, both of United Kingdom

[73] Assignee: Merck Sharp & Dohme Limited, Hoddesdon, United Kingdom

[21] Appl. No.: 09/006,028

[22] Filed: Jan. 12, 1998

[30] Foreign Application Priority Data

Jan. 13, 1997 [GB] United Kingdom ............ 97005557

[51] Int. Cl.$^6$ ................................ A01N 43/78
[52] U.S. Cl. .................. 514/365; 514/370; 514/372; 514/381; 514/382; 514/383; 514/649; 514/655; 514/255; 514/256; 514/340; 514/352; 514/357; 514/364; 514/374; 514/377; 514/378; 514/380; 514/398; 514/399; 514/406; 548/131; 548/143; 548/190; 548/198; 548/202; 548/205; 548/235; 548/247; 548/251; 548/254; 548/255; 548/262.2; 548/264.8; 548/265.6; 548/265.8; 548/266.2; 548/267.2; 548/269.4; 548/377.1; 544/336; 544/242; 546/304; 546/329; 549/480; 549/491; 564/367; 564/372; 564/384
[58] Field of Search ................ 514/381, 655, 514/365, 372, 383; 548/250, 269.4, 255, 202, 205; 564/372, 384

[56] References Cited

U.S. PATENT DOCUMENTS

| | | | |
|---|---|---|---|
| 5,521,220 | 5/1996 | O'Neill | 514/649 |
| 5,612,337 | 3/1997 | Baker et al. | 514/236.2 |
| 5,719,147 | 2/1998 | Dorn et al. | 514/227.5 |

*Primary Examiner*—Johann Richter
*Assistant Examiner*—Jane C. Oswecki
*Attorney, Agent, or Firm*—J. Eric Thies; David L. Rose

[57] ABSTRACT

The present invention provides a compound of formula:

(I)

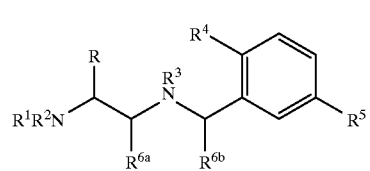

wherein R, $R^1$, $R^2$, $R^3$, $R^4$, $R^5$, $R^{6a}$ and $R^{6b}$ are defined herein or a pharmaceutically acceptable salt thereof, a process for its preparation, intermediates and its use as a tachykinin antagonist.

7 Claims, No Drawings

ETHANE-1-2-DIAMINE DERIVATIVES AND TACHYKININ ANTAGONISTS

CROSS REFERENCE TO RELATED APPLICATIONS

This application claims priority from Great Britain Application No. 9700555.7, filed Jan. 13, 1997.

This invention relates to a class of compounds which are useful as tachykinin antagonists.

The tachykinins are a group of naturally occurring peptides found widely distributed throughout mammalian tissues, both within the central nervous system and in peripheral nervous and circulatory systems.

At present, there are three known mammalian tachykinins referred to as substance P, neurokinin A (NKA, substance K, neuromedin L) and neurokinin B (NKB, neuromedin K) (for review see J. E. Maggio, *Peptides* (1985) 6(suppl. 3), 237–242). The current nomenclature designates the three tachykinin receptors mediating the biological actions of substance P, NKA and NKB as the $NK_1$, $NK_2$ and $NK_3$ receptors, respectively.

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases, proliferative vitreoretinopathy, irritable bowel syndrome and disorders of bladder function including cystitis and bladder detrusor hyper-reflexia is reviewed in "Tachykinin Receptors and Tachykinin Receptor Antagonists", C. A. Maggi, R. Patacchini, P. Rovero and A. Giachetti, *J. Auton. Pharmacol.* (1993) 13, 23–93.

For instance, substance P is believed inter alia to be involved in the neurotransmission of pain sensations [Otsuka et al, "Role of Substance P as a Sensory Transmitter in Spinal Cord and Sympathetic Ganglia" in 1982 *Substance P in the Nervous System*, Ciba Foundation Symposium 91, 13–34 published by Pitman) and Otsuka and Yanagisawa, "Does Substance P Act as a Pain Transmitter?" *TIPS* (1987) 8, 506–510], specifically in the transmission of pain in migraine (B. E. B. Sandberg et al, *J. Med Chem*, (1982) 25, 1009) and in arthritis [Levine et al *Science* (1984) 226, 547–549]. Tachykinins have also been implicated in gastrointestinal (GI) disorders and diseases of the GI tract such as inflammatory bowel disease [Mantyh et al *Neuroscience* (1988) 25(3), 817–37 and D. Regoli in "*Trends in Cluster Headache*" Ed. Sicuteri et al Elsevier Scientific Publishers, Amsterdam (1987) page 85)] and emesis [F. D. Tattersall et al, *Eur. J. Pharmacol.*, (1993) 250, R5–R6]. It is also hypothesised that there is a neurogenic mechanism for arthritis in which substance P may play a role [Kidd et al "A Neurogenic Mechanism for Symmetrical Arthritis" in *The Lancet*, Nov. 11, 1989 and Grönblad et al, "Neuropeptides in Synovium of Patients with Rheumatoid Arthritis and Osteoarthritis" in *J. Rheumatol.* (1988) 15(12), 1807–10]. Therefore, substance P is believed to be involved in the inflammatory response in diseases such as rheumatoid arthritis and osteoarthritis, and fibrositis [O'Byrne et al, *Arthritis and Rheumatism* (1990) 33, 1023–8]. Other disease areas where tachykinin antagonists are believed to be useful are allergic conditions [Hamelet et al, *Can. J. Pharmacol.* *Physiol.* (1988) 66, 1361–7], immunoregulation [Lotz et al, *Science* (1988) 241, 1218–21 and Kimball et al, *J. Immunol.* (1988) 141(10), 3564–9] vasodilation, bronchospasm, reflex or neuronal control of the viscera [Mantyh et al, *PNAS* (1988) 85, 3235–9] and, possibly by arresting or slowing β-amyloid-mediated neurodegenerative changes [Yankner et al, *Science* (1990) 250, 279–82] in senile dementia of the Alzheimer type, Alzheimer's disease and Down's Syndrome.

Tachykinin antagonists may also be useful in the treatment of small cell carcinomas, in particular small cell lung cancer (SCLC) [Langdon et al, *Cancer Research* (1992) 52, 4554–7].

Substance P may also play a role in demyelinating diseases such as multiple sclerosis and amyotrophic lateral sclerosis [J. Luber-Narod et al, poster *C.I.N.P. XVIIth Congress*, Jun. 28th–Jul. 2nd 1992], and in disorders of bladder function such as bladder detrusor hyper-reflexia (Lancet, May 16th 1992, 1239).

It has furthermore been suggested that tachykinins have utility in the following disorders: depression, dysthymic disorders, chronic obstructive airways disease, hypersensitivity disorders such as poison ivy, vasospastic diseases such as angina and Reynaud's disease, fibrosing and collagen diseases such as scleroderma and eosinophilic fascioliasis, reflex sympathetic dystrophy such as shoulderthand syndrome, addiction disorders such as alcoholism, stress related somatic disorders, neuropathy, neuralgia, disorders related to immune enhancement or suppression such as systemic lupus erythematosus (European patent specification no. 0 436 334), ophthalmic disease such as conjunctivitis, vernal conjunctivitis, and the like, and cutaneous diseases such as contact dermatitis, atopic dermatitis, urticaria, and other eczematoid dermatitis (European patent specification no. 0 394 989).

The present invention provides a compound of formula (I):

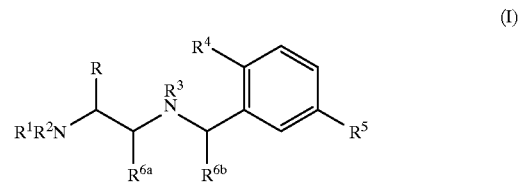

where:
R is phenyl or benzhydryl in which the or each phenyl moiety is optionally substituted by from 1 to 3 substituents independently chosen from $C_{1-6}$alkyl, $C_{2-6}$alkenyl, $C_{2-6}$alkynyl, halogen, cyano, nitro, trifluoromethyl, trimethylsilyl, $SR^a$, $SOR^a$, $SO_2R^a$, $OR^a$, $NR^aR^b$, $NR^aCOR^b$, $NR^aCOOR^b$ or $CONR^aR^b$, where each of $R^a$ and $R^b$ is independently hydrogen, $C_{1-6}$alkyl, phenyl or trifluoromethyl;

$R^1$ is hydrogen or $(CH_2)_p$—Het where Het is a 5- or 6-membered aromatic heterocyclic group containing 1, 2 or 3 nitrogen atoms optionally substituted by =O or =S and optionally substituted by a group of the formula $ZNR^7R^8$;

$R^2$ is hydrogen, $C_{1-6}$alkyl or $C_{1-4}$alkoxy$C_{1-6}$alkyl;

$R^3$ is hydrogen, $C_{1-6}$alkyl or $C_{1-6}$alkylcarbonyl;

$R^4$ is $C_{1-6}$alkyl, fluoro$C_{1-6}$alkyl, $C_{1-6}$alkoxy, fluoro$C_{1-6}$alkoxy, $C_{1-6}$alkoxy$C_{1-4}$alkyl, fluoro$C_{1-6}$alkoxy$C_{1-4}$alkyl, $C_{2-6}$alkenyloxy, $C_{3-7}$cycloalkoxy, phenoxy, benzyloxy, cyano, halogen or NR$^d$R$^e$ where each of R$^d$ and R$^e$ is independently hydrogen or C$_{1-4}$alkyl;

R$^5$ is fluoroC$_{1-6}$alkoxy or (CH$_2$)$_q$Het$^1$ where Het$^1$ is a 5- or 6-membered aromatic heterocyclic group containing 1, 2, 3 or 4 heteroatoms chosen from nitrogen, oxygen and sulphur, which group is optionally substituted by one or two groups chosen from C$_{1-6}$alkyl, C$_{1-6}$alkoxy, C$_{3-7}$cycloalkyl, C$_{3-7}$cycloalkylC$_{1-4}$alkyl, trifluoromethyl, OCF$_3$, NO$_2$, CN, SR$^a$, SOR$^a$, SO$_2$R$^a$, COR$^a$, CO$_2$R$^a$, phenyl, —(CH$_2$)$_r$NR$^a$R$^b$, —(CH$_2$)$_p$NR$^a$R$^b$, —(CH$_2$)$_r$CON$^a$R$^b$ or —(CH$_2$)C(O)R$^a$, where R$^a$ and R$^b$ are independently as defined above;

R$^{6a}$ and R$^{6b}$ are independently hydrogen or C$_{1-6}$alkyl;

R$^7$ is hydrogen or C$_{1-4}$alkyl, C$_{3-7}$cycloalkyl, C$_{3-7}$cycloalkylC$_{1-4}$alkyl, or C$_{2-4}$alkyl substituted by C$_{1-4}$alkoxy or hydroxyl;

R$^8$ is hydrogen or C$_{1-4}$alkyl, C$_{3-7}$cycloalkyl, C$_{3-7}$cycloalkylC$_{1-4}$alkyl, or C$_{2-4}$alkyl substituted by C$_{1-4}$alkoxy, hydroxyl or a 4, 5 or 6 membered heteroaliphatic ring containing one or two heteroatoms selected from N, O and S;

or R$^7$, R$^8$ and the nitrogen atom to which they are attached form a heteroaliphatic ring of 4 to 7 ring atoms, optionally substituted by one or two groups selected from hydroxy or C$_{1-4}$alkoxy optionally substituted by a C$_{1-4}$alkoxy or hydroxyl group, and optionally containing a double bond, which ring may optionally contain an oxygen or sulphur ring atom, a group S(O) or S(O)$_2$ or a second nitrogen atom which will be part of a NH or NR$^c$ moiety where R$^c$ is C$_{1-4}$alkyl optionally substituted by hydroxy or C$_{1-4}$alkoxy;

or R$^7$, R$^8$ and the nitrogen atom to which they are attached form a non-aromatic azabicyclic ring system of 6 to 12 ring atoms;

Z is C$_{1-6}$alkylene or C$_{3-6}$cycloalkyl;

p is from 1 to 6; and q and r are independently zero, one or two;

or a pharmaceutically acceptable salt or prodrug thereof.

Preferred compounds are those in which:

R is optionally substituted phenyl or unsubstituted benzhydryl;

R$^1$ is hydrogen or a group CH$_2$—Het where Het is as defined above;

R$^2$ is hydrogen, C$_{1-4}$alkyl or C$_{1-2}$alkoxyC$_{1-4}$alkyl;

R$^3$ is hydrogen or C$_{1-6}$alkylcarbonyl;

R$^4$ is methyl, trifluoromethyl, methoxy, ethoxy, isopropoxy or trifluoromethoxy; and R$^5$ is trifluoromethoxy or optionally substituted furan, pyridine, pyrazole, imidazole, oxazole, isoxazole, pyrazine, pyrimidine, thiazole, 1,2,3-triazole, 1,2,4-triazole, 1,2,4-oxadiazole, 1,3,4-oxadiazole or tetrazole.

It will be understood that the following preferred definition of the various substituents apply to the generic formula for compounds of the present invention as well as to the preferred class of compounds mutatis mutandis.

R is preferably optionally substituted phenyl or unsubstituted benzhydryl and more preferably unsubstituted phenyl or unsubstituted benzhydryl.

R$^1$ is preferably hydrogen or a group CH$_2$—Het where Het is as defined above, more preferably hydrogen or a group CH$_2$—Het wherein Het contains one, two or three nitrogen atoms and is optionally substituted as described above, and even more preferably hydrogen or a group —CH$_2$—Het wherein Het is

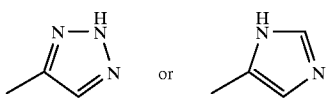

optionally substituted as described above preferably at a carbon atom. Most preferably R$^1$ is hydrogen.

R$^2$ is preferably hydrogen, C$_{1-4}$alkyl or C$_{1-2}$alkoxyC$_{1-4}$alkyl, more preferably hydrogen, methyl, ethyl, propyl or methoxyethyl and most preferably hydrogen.

R$^3$ is preferably hydrogen or C$_{1-6}$alkylcarbonyl, more preferably hydrogen or C$_{1-4}$alkylcarbonyl, even more preferably hydrogen or methylcarbonyl and most preferably hydrogen.

R$^4$ is preferably methyl, trifluoromethyl, methoxy, ethoxy, isopropoxy or trifluoromethoxy, more preferably methoxy or trifluoromethoxy and most preferably methoxy.

R$^5$ is preferably trifluoromethoxy or optionally substituted furan, pyridine, pyrazole, imidazole, oxazole, isoxazole, pyrazine, pyrimidine, thiazole, 1,2,3-triazole, 1,2,4-triazole, 1,2,4-oxadiazole, 1,3,4-oxadiazole or tetrazole, and more preferably trifluoromethoxy or optionally substituted tetrazole where the substituent is preferably trifluoromethyl. More preferably still, R$^5$ is trifluoromethoxy,

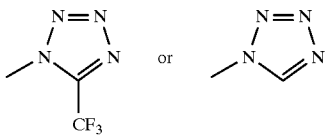

and is most preferably

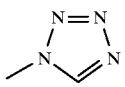

q is preferably zero.

R$^{6a}$ and R$^{6b}$ are preferably independently chosen from hydrogen and methyl. More preferably both are hydrogen.

Particularly suitable moieties ZNR$^7$R$^8$ include those wherein Z is CH$_2$ or (CH$_2$)$_2$ and NR$^7$R$^8$ is amino, methylamino, dimethylamino, diethylamino, azetidinyl, pyrrolidino and morpholino. In particular, Z is preferably CH$_2$ and NR$^7$R$^8$ is preferably dimethylamino, azetidinyl or pyrrolidine, especially dimethylamino.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

As used herein, the terms "fluoroC$_{1-6}$alkyl" and "fluoroC$_{1-6}$alkoxy" means a C$_{1-6}$alkyl or C$_{1-6}$alkoxy group in which one or more (in particular, 1 to 3) hydrogen atoms have been replaced by a fluorine atom. Particularly preferred are fluoroC$_{1-3}$alkyl and fluoroC$_{1-3}$alkoxy groups, for example, CF$_3$, CH$_2$CH$_2$F, CH$_2$CHF$_2$, CH$_2$CF$_3$, OCF$_3$, OCH$_2$CH$_2$F, OCH$_2$CHF$_2$ or OCH$_2$CF$_3$, and most especially CF$_3$, OCF$_3$ and OCH$_2$CF$_3$.

The cycloalkyl groups referred to herein may represent, for example, cyclopropyl, cyclobutyl, cyclopentyl or cyclohexyl.

Similarly cycloalkoxy groups referred to herein may represent, for example, cyclopropoxy or cyclobutoxy.

As used herein, the terms "alkenyl" and "alkynyl" as a group or part of a group means that the group is straight or branched. Examples of suitable alkenyl groups include vinyl and allyl. A suitable alkynyl group is propargyl.

As used herein the term "halogen" means fluorine, chlorine, bromine or iodine. The preferred halogens are fluorine and chlorine of which fluorine is preferred, unless otherwise stated.

Examples of protecting groups are butoxycarbonyl and benzyloxycarbonyl.

Specific compounds within the scope of this invention include those in which: R is phenyl, $R^1$, $R^2$ and $R^3$ are hydrogen, $R^4$ is methoxy, $R^5$ is

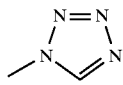

and $R^{6a}$ and $R^{6b}$ are hydrogen; or

R is benzhydryl, $R^1$, $R^2$ and $R^3$ are hydrogen, $R^4$ is methoxy, $R^5$ is

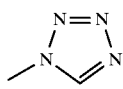

and $R^{6a}$ and $R^{6b}$ are hydrogen.

Particularly favoured compounds are:

$N^2$-(2-methoxy-5-tetrazol-1-yl-benzyl)-1-phenylethane-1,2-diamine; and $N^1$-(2-methoxy-5-tetrazol-1-y-benzyl)-3,3-diphenylpropane-1,2-diamine;

and the salts and prodrugs thereof

In a further aspect of the present invention, the compounds of formula (I) may be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The compounds according to the invention have at least one asymmetric centre and may accordingly exist both as enantiomers and as diastereoisomers. It is to be understood that all such isomers and mixtures thereof are encompassed within the scope of the present invention.

The present invention further provides pharmaceutical compositions comprising one or more compounds of formula (I) and a pharmaceutically acceptable carrier or excipient.

Preferably the compositions according to the invention are in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising a compound of formula (I), as the active ingredient, in association with a surface-active agent (or wetting agent or surfactant) or in the form of an emulsion (as a water-in-oil or oil-in-water emulsion).

Suitable surface-active agents include, in particular, non-ionic agents, such as polyoxyethylenesorbitans (e.g. TWEEN™ 20 [polyoxyethylenesorbitan monolaurate], TWEEN™ 40 [polyoxyethylenesorbitan monopalmitate], TWEEN™ 60 [polyoxyethylenesorbitan monostearate], TWEEN™ 80 [polyoxyethylenesorbitan monooleate] or TWEEN™ 85 [polyoxyethylenesorbitan trioleate]) and other sorbitans (e.g. SPAN™ 20 [sorbitan monolaurate], SPAN™ 40 [sorbitan monopalmitate], SPAN™ 60 [sorbitan monostearate], SPAN™ 80 [sorbitan monooleate]or SPAN™ 85 [sorbitan trioleate]). All grades of TWEEN™ and SPAN™ are available from Sigma Chemical Company Ltd., St. Louis, Mo. Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as INTRALIPID™ (soybean oil 10% or 20%; egg phospholipids; glycerol; and water [available from Cutter Laboratories, Berkeley, Calif. or Vitrum AG, Stockholm, Sweden]), LIPOSYN™ (safflower oil; egg phospholipids; gylcerol; and water [available from Abbott Laboratories, North Chicago, Ill.]), INFONUTROL™, (cottonseed oil; soybean phospholipids; glucose; Pluronic F-68; and water [available from Astra-Hewlett, Södertäye, Sweden]), LIPOFUNDIN™ (cottonseed oil; soybean phospholipids; sorbitol; and water [available from Braun, Melsunger, Germany]), and LIPIPHYSAN™ (cottonseed oil 10% or 15%; soybean lecithin; sorbitol; DL-α-tocopherol; and water [available from Egic, L'Equilibre Biologique SA, Loiret, France]). The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion will preferably comprise fat droplets between 0.1 and 1.0 $\mu$m, particularly 0.1 and 0.5 $\mu$m, and have a pH in the range of 5.5 to 8.0.

Particularly preferred emulsion compositions are those prepared by mixing a compound of formula (I) with INTRALIPID™ (soybean oil 10% or 20%; egg phospholipids; glycerol; and water [available from Cutter Laboratories, Berkeley, Calif. or Vitrum AG, Stockholm, Sweden]), or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal Arespiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention further provides a process for the preparation of a pharmaceutical composition comprising a compound of formula (I), which process comprises admixing a compound of formula (I) and a pharmaceutically acceptable carrier or excipient.

The compounds of formula (I) are of value in the treatment of a wide variety of clinical conditions which are characterised by the presence of an excess of tachykinin, in particular substance P, activity.

Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delirium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple aetiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delirium, withdrawal delirium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compounds of the present invention will therefore be of use in the prevention or treatment of diseases and conditions in which pain predominates, including soft tissue and peripheral damage, such as acute trauma, osteoarthritis, rheumatoid arthritis, musculo-skeletal pain, particularly after trauma, spinal pain, dental pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis.

Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastrooesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythmatosus; plasma extravasation resulting from cytokine chemotherapy, disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine.

The compounds of formula (I) are also of value in the treatment of a combination of the above conditions, in particular in the treatment of combined post-operative pain and post-operative nausea and vomiting.

The compounds of formula (I) are particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents, including those routinely used in cancer chemotherapy, and emesis induced by other pharmacological agents, for example, rolipram.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *Nausea and Vomiting: Recent Research and Clinical Advances*, Eds. J. Kucharczyk et al, CRC Press Inc., Boca Raton, Fla., USA (1991) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172].

The compounds of formula (I) are also of use in the treatment of emesis induced by radiation including radiation therapy such as in the treatment of cancer, or radiation sickness; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a $5\text{-HT}_3$ antagonist, such as ondansetron, granisetron or tropisetron, or other anti-emetic medicaments, for example, a dopamine antagonist such as metoclopramide. Additionally, a compound of formula (I) may be administered in combination with an anti-inflammatory corticosteroid, such as dexamethasone. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

Compounds of the present invention may be tested in the ferret model of cisplatin-induced emesis described by F. D. Tattersall et al, in *Eur. J. Pharmacol.*, (1993) 250, R5–R6, to demonstrate attenuation of the retching and vomiting induced by cisplatin.

The compounds of formula (I) are also particularly useful in the treatment of pain or nociception and/or inflammation and disorders associated therewith such as, for example, neuropathy, such as diabetic and chemotherapy-induced neuropathy, postherpetic and other neuralgias, asthma, osteoarthritis, rheumatoid arthritis and headache, including migraine, acute or chronic tension headache, cluster headache, temporomandibular pain, and maxillary sinus pain.

The present invention further provides a compound of formula (I) for use in a method of treatment of the human or animal body.

According to a further or alternative aspect, the present invention provides a compound of formula (I) for use in the manufacture of a medicament for the treatment of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of a compound of formula (I) or a composition comprising a compound of formula (I).

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a $\beta_2$-adrenergic receptor agonist or tachykinin antagonist which acts at NK-2 receptors. The compound of formula (I) and the bronchodilator may be administered to a patient simultaneously, sequentially or in combination.

Likewise, a compound of the present invention may be employed with a leukotriene antagonists, such as a leukotriene $D_4$ antagonist such as a compound selected from those disclosed in European patent specification nos. 0 480 717 and 0 604 114 and in U.S. Pat. Nos. 4,859,692 and 5,270,324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

It will be appreciated that for the treatment or prevention of migraine, a compound of the present invention may be used in conjunction with other anti-migraine agents, such as ergotamines or 5-$HT_1$ agonists, especially sumatriptan.

Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an anti-inflammatory agent such as a bradykinin receptor antagonist.

The present invention also provides a composition comprising a compound of formula (I), a bronchodilator, and a pharmaceutically acceptable carrier.

It will be appreciated that for the treatment or prevention of pain or nociception, a compound of the present invention may be used in conjunction with other analgesics, such as acetaminophen (paracetamol), aspirin and other NSAIDs and, in particular, opioid analgesics, especially morphine. Specific anti-inflammatory agents include diclofenac, ibuprofen, indomethacin, ketoprofen, naproxen, piroxicam and sulindac. Suitable opioid analgesics of use in conjunction with a compound of the present invention include morphine, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine; or a pharmaceutically acceptable salt thereof. Preferred salts of these opioid analgesics include morphine sulphate, morphine hydrochloride, morphine tartrate, codeine phosphate, codeine sulphate, dihydrocodeine bitartrate, diacetylmorphine hydrochloride, hydrocodone bitartrate, hydromorphone hydrochloride, levorphanol tartrate, oxymorphone hydrochloride, alfentanil hydrochloride, buprenorphine hydrochloride, butorphanol tartrate, fentanyl citrate, meperidine hydrochloride, methadone hydrochloride, nalbuphine hydrochloride, propoxyphene hydrochloride, propoxyphene napsylate (2-naphthalenesulphonic acid (1:1) monohydrate), and pentazocine hydrochloride.

Therefore, in a further aspect of the present invention, there is provided a pharmaceutical composition comprising a compound of the present invention and an analgesic, together with at least one pharmaceutically acceptable carrier or excipient.

In a further or alternative aspect of the present invention, there is provided a product comprising a compound of the present invention and an analgesic as a combined preparation for simultaneous, separate or sequential use in the treatment or prevention of pain or nociception.

For the treatment of motion sickness, a compound of the present invention may be used in conjunction with a muscarinic antagonist and/or an antihistamine.

Suitable muscarinic antagonists of use in the present invention include scopolamine (ι-hyoscine); or a pharmaceutically acceptable salt thereof A preferred salt of ι-hyoscine is the hydrobromide salt. Suitable antihistamines include buclizine, chlorcyclizine, cinnarizine, cyclizine, dimenhydrinate, diphenhydramine, flunarizine, meclozine, pheniramine, promnethazine and propiomazine; or a pharmaceutically acceptable salt thereof.

Preferred salts of antihistamines include buclizine hydrochloride, chlorcyclizine hydrochloride, cyclizine hydrochloride, cylizine lactate, cyclizine tartrate, diphenhydramine citrate, diphenhydramine di(acefyllinate) [bis (theophyllin-7-ylacetate)], diphenhydramine hydrochloride, flunarizine hydrochloride, meclozine hydrochloride, pheniramine aminosalicylate, pheniramine maleate, promethazine hydrochloride, promethazine theoclate, propiomazine hydrochloride and propiomazine maleate.

A further class of compound with antihistamine and pronounced anti-muscarinic activity are phenothiazines and related compounds. Promethazine is the archetypal phenothiazine. Other examples include chlorpromazine, methotimeprazine, perphenazine, prochlorperazine and trifluoperazine; and pharmaceutically acceptable salts thereof.

Preferred salts of the phenothiazines include promethazine hydrochloride, promethazine theoclate, chlorpromethazine hydrochloride, prochlorperazine maleate and prochlorperazine mesylate.

Particularly preferred antihistamines of use in conjunction with a compound of the present invention include cinnarizine, cyclizine, dimenhydrinate, meclizine and promethazine; or a pharmaceutically acceptable salt thereof A compound of the present invention and a muscarinic antagonist and/or an antihistamine may be formulated in a single pharmaceutical composition or alternatively in individual pharmaceutical compositions for isimultaneous, separate or sequential use in accordance with a further aspect of the present invention.

The excellent pharmacological profile of the compounds of the present invention offers the opportunity for their use in therapy at low doses thereby minimising the risk of unwanted side effects.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis using an injectable formulation, a suitable dosage level is about 0.001 to 10 mg/kg per day, preferably about 0.005 to 5 mg/kg per day, and especially 0.01 to 1 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

According to a general process (A), compounds of the present invention may be prepared by reacting a compound of formula (II):

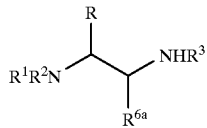

(II)

where $R$, $R^1$, $R^2$, $R^3$ and $R^{6a}$ are as defined above with the exception that $R^1$ may be a protecting group such as benzyloxycarbonyl, with a compound of formula (III):

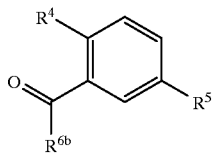

(III)

where $R^4$, $R^5$, and $R^{6b}$ as defined above, followed by addition of a reducing agent, such as sodium cyanoborohydride, and then removing any protecting groups if present, for example by hydrogenation in a solvent such as ethanol over $Pd(OH_2)/C$.

The reaction between compounds of formulae (II) and (III) is typically carried out in a solvent such as methanol, generally in the presence of a catalyst such as a molecular sieve in the presence of an acid such as citric acid and generally for about 30 minutes.

According to another general process (B), compounds of the present invention may be prepared by reacting a compound of formula (I) in which $R^1$ is hydrogen, hereinafter referred to as a compound of formula (IV):

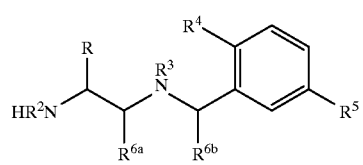

(IV)

wherein $R$, $R^2$, $R^3$, $R^4$, $R^5$, $R^{6a}$ and $R^{6b}$ are as defined in relation to formula (I), with a compound of formula (V):

(V)

wherein $R^{1a}$ is a group of the formula $(CH_2)_p$—Het as defined in relation to formula (I) or a precursor therefor, and LG is a leaving group such as an alkyl or arylsulphonyloxy group (e.g. mesylate or tosylate) or a halogen atom (e.g. bromine, chlorine or iodine); and if $R^{1a}$ is a precursor group, converting it to the group $(CH_2)_p$—Het (in which process any reactive group may be protected and thereafter deprotected if desired).

This reaction may be performed in a conventional manner, for example, in an organic solvent such as dimethylformamide in the presence of an acid acceptor such as potassium carbonate.

According to another general process (C), compounds of the present invention in which $R^5$ is a tetrazol-1-yl group and p is zero may be prepared by the reaction of a compound of formula (VI):

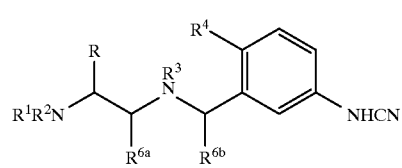

(VI)

wherein $R$, $R^1$, $R^2$, $R^3$, $R^4$, $R^{6a}$ and $R^{6b}$ are as defined in relation to formula (I), with ammonium chloride and sodium azide at elevated temperature, conveniently in a solvent such as dimethylformamide.

According to another general process (D), compounds of the present invention may be prepared by a coupling reaction between a compound of formula (VII) and a compound of formula (VIII):

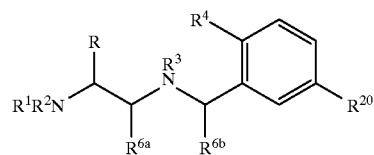

(VII)

(VIII)

wherein $R$, $R^1$, $R^2$, $R^3$, $R^4$, $R^5$, $R^{6a}$ and $R^{6b}$ are defined in relation to formula (I) and one of $R^{20}$ and $R^{21}$ is $B(OH)_2$ or $Sn(alkyl)_3$ or a derivative thereof, and the other is a leaving group such as a halogen atom (e.g. bromine or iodine) or —$OSO_2CF_3$. Where one of $R^{20}$ and $R^{21}$ is $B(OH)_2$, the reaction is conveniently effected in the presence of a palladium (0) catalyst such as tetrakis(triphenylphosphine)

palladium(0) in a suitable solvent such as an ether, for example, dimethoxyethane, at an elevated temperature. Where one of $R^{20}$ and $R^{21}$ is $Sn(alkyl)_3$, the reaction is conveniently effected in the presence of a palladium (II) catalyst such as bis(triphenylphosphine)palladium(II) chloride, in a suitable solvent such as an aromatic hydrocarbon, for example, toluene, at an elevated temperature.

The compounds of formulae (II) and (III) can be made by known methods.

The compounds of formula (IV) can be made by reaction of a compound of formula (III) with a compound of formula (IX):

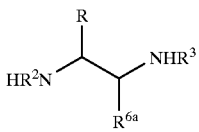

(IX)

wherein R, $R^2$, $R^3$ and $R^{6a}$ are as defined in relation to formula (I), which is made in the same way as compounds of formula (II) in which $R^1$=H.

Compounds of formula (VI) can be made by reaction of a compound of formula (II) with a compound of formula (X):

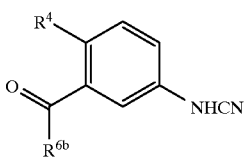

(X)

wherein $R^4$ and $R^{6a}$ are as defined in relation to formula (I), which are made in an analogous manner to compounds of formula (III).

Compounds of formula (VII) are made by reaction of a compound of formula (II) with a compound of formula (XI):

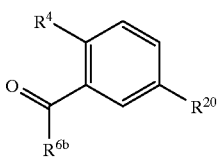

(XI)

wherein $R^{6b}$ and $R^{20}$ are as defined in relation to formula (VII), in an analogous manner to compounds of formula (III).

Compounds of formula (IV), (VIII), (IX), (X) and (XI) are known or may be prepared by procedures which will be readily apparent to one skilled in the art.

Further details of suitable procedures will be found in the accompanying Examples.

Compounds of formula I in which $R^1$ represents a protecting group, for example butoxycarbonyl, are a further feature of the present invention.

Further useful methodology for the preparation of compounds in which $R^1$ is a $(CH_2)_p$—Het is described, for example, in International Patent Specification No. WO 95/18124.

It will be appreciated that compounds of the formula (I) wherein Het contains an =O or =S substituent can exist in tautomeric forms. All such tautomeric forms and mixtures thereof are included within this invention. Most aptly the =O or =S substituent in Het is the =O substituent.

Where they are not commercially available, the intermediates of formula (V) above may be prepared by the procedures described in the accompanying Examples or by alternative procedures which will be readily apparent to one skilled in the art.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds were found to be active with $IC_{50}$ at the $NK_1$ receptor of less than 1 µM on said test method.

The following non-limiting Examples serve to illustrate the preparation of compounds of the present invention.

EXAMPLE 1

$N^2$-(2-methoxy-5-tetrazol-1-yl-benzyl)-1-phenylethane-1,2-diamine

Step 1 [2-(2-methoxy-5-tetrazol-1-yl-benzylamino)-1-phenylethyl] carbamic acid benzyl ester $N^\beta$-[(Benzyloxy)carbonyl] (R,S)-β-amino-2-phenylethanamine (0.6 g, 2.2 mmol) obtained as described in Horwell et al., J. Med. Chem., 1991, 34, 404–414 and 2-methoxy-5-(tetrazol-1-yl)benzaldehyde and (0.42 g, 2.2 mmol) were dissolved in methanol (10 ml). Molecular sieves and citric acid (0.85 g, 4.4 mmol) were added and the reaction mixture was stirred for 30 mins. Sodium cyanoborohydride (0.14 g, 2.2 mmol) was then added and the reaction mixture was stirred for a further 30 mins before being filtered and partitioned using ethyl acetate/sodium bicarbonate solution. The organic layer was washed with water, dried over $MgSO_4$ and then the solvent was evaporated off in vacuo. The product was purified using gravity silica column using 100% dichloromethane followed by 5% MeOH/0.1% $NH_4OH$/DCM to elute to give the above benzyl ester. The following data was obtained:

$^1$H NMR (360 MHz, $CDCl_3$) δ 3.87 (3H, s), 3.94–4.26 (3H, m), 5.04 (4H, m), 7.02 (1H, d, J=8.5 Hz), 7.26–7.32 (10H, m), 7.69–7.76 (2H, m), 9.12 (1H, s). Mass spec $ES^+$ (M+1)=459.

Step 2 $N^2$-(2-methoxy-5-tetrazol-1-yl-benzyl)-1-phenylethane-1,2-diamine 0.2 g, 0.56 mmol of the product of step 1 was hydrogenated using $Pd(OH_2)/C$ in ethanol (40 ml) at 50 psi for 16 hours. The reaction mixture was filtered and the solvent was evaporated off in vacuo. The crude product was purified using a gravity silica column using 0.1% $NH_4OH$/2–5% MeOH/DCM to elute to give the title compound. The following data was obtained:

$^1$H NMR (250 MHz, $CDCl_3$) δ 2.77–2.94 (1H, m), 3.86 (3H, s), 3.89 (2H, s), 4.11 (1H, m), 6.98 (1H, d, J=8.5 Hz), 7.24–7.35 (5H, m), 7.55–7.61 (2H, m), 8.96 (1H, s). Mass spec $ES^+$ (M+1)=325.

EXAMPLE 2

$N^1$-(2-methoxy-5-tetrazol-1-yl-benzyl)-3,3-diphenylpropane-1,2-diamine

The title compound was synthesized in an analogous fashion to Example 1 starting from +/−diphenylalaninol prepared as described in Williams et al *Bioorg. Med. Chem. Lett* 1994, 4, 1903.

$^1$H NMR (250 MHz, CDCl$_3$) δ 2.4 (1H, m), 2.65 (1H, m), 3.71–3.80 (4H, m), 3.87 (3H, s), 6.96 (1H, d, J=8.3 Hz), 7.07–7.38 (10H, m), 7.55 (2H, m), 8.96 (1H, s). Mass spec ES$^+$ (M+1)=415.

We claim:

1. A compound of formula (I):

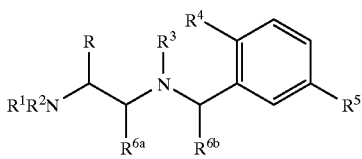

(I)

where:
- R is phenyl or benzhydryl in which the or each phenyl moiety is optionally substituted by from 1 to 3 substituents independently chosen from $C_{1-6}$alkyl, $C_{2-6}$alkenyl, $C_{2-6}$alkynyl, halogen, cyano, nitro, trifluoromethyl, trimethylsilyl, SR$^a$, SOR$^a$, SO$_2$R$^a$, OR$^a$, NR$^a$R$^b$, NR$^a$COR$^b$, NR$^a$COOR$^b$ or CONR$^a$R$^b$, where each of R$^a$ and R$^b$ is independently hydrogen, $C_{1-6}$alkyl, phenyl or trifluoromethyl;
- R$^1$ is hydrogen or (CH$_2$)$_p$—Het where Het is a 5-membered aromatic heterocyclic group containing 3 or 4 nitrogen atoms, or 1 nitrogen and 1 sulfur atom optionally substituted by =O or =S and optionally substituted by a group of the formula ZNR$^7$R$^8$;
- R$^2$ is hydrogen, $C_{1-6}$alkyl or $C_{1-4}$alkoxy$C_{1-6}$alkyl;
- R$^3$ is hydrogen, $C_{1-6}$alkyl or $C_{1-6}$alkylcarbonyl;
- R$^4$ is $C_{1-6}$alkyl, fluoro$C_{1-6}$alkyl, $C_{1-6}$alkoxy, fluoro$C_{1-6}$alkoxy, $C_{1-6}$alkoxy$C_{1-4}$alkyl, fluoro$C_{1-6}$alkoxy$C_{1-4}$alkyl, $C_{2-6}$alkenyloxy, $C_{3-7}$cycloalkoxy, phenoxy, benzyloxy, cyano, halogen or NR$^d$R$^e$ where each of R$^d$ and R$^e$ is independently hydrogen or $C_{1-4}$alkyl;
- R$^5$ is fluoro$C_{1-6}$alkoxy or (CH$_2$)$_q$Het$^1$ where Het$^1$ is a 5-membered aromatic heterocyclic group which is selected from tetrazole, triazole and thiazole and which group is optionally substituted by one or two groups chosen from $C_{1-6}$alkyl, $C_{1-6}$alkoxy, $C_{3-7}$cycloalkyl, $C_{3-7}$cycloalkyl$C_{1-4}$alkyl, trifluoromethyl, OCF$_3$, NO$_2$, CN, SR$^a$, SOR$^a$, SO$_2$R$^a$, COR$^a$, CO$_2$R$^a$, phenyl, —(CH$_2$)$_r$NR$^a$R$^b$, —(CH$_2$)$_r$NR$^a$R$^b$, —(CH$_2$)$_r$CON$^a$R$^b$ or —(CH$_2$)C(O)R$^a$, where R$^a$ and R$^b$ are independently as defined above;
- R$^{6a}$ and R$^{6b}$ are independently hydrogen or $C_{1-6}$alkyl;
- R$^7$ is hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy or hydroxyl;
- R$^8$ is hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy, hydroxyl or a 5 membered ring selected from the group consisting of tetrazole, triazole and thiazole;
- or R$^7$, R$^8$ and the nitrogen atom to which they are attached form a ring of 5 ring atoms, optionally substituted by one or two groups selected from hydroxy or $C_{1-4}$alkoxy optionally substituted by a $C_{1-4}$alkoxy or hydroxyl group, and optionally containing a double bond, which ring may optionally contain a sulphur ring atom, a group S(O) or S(O)$_2$ or two or three additional nitrogen atoms which will be part of a NH or NR$^c$ moiety where R$^c$ is $C_{1-4}$alkyl optionally substituted by hydroxy or $C_{1-4}$alkoxy;
- Z is $C_{1-6}$alkylene or $C_{3-6}$cycloalkyl;
- p is from 1 to 6; and
- q and r are independently zero, one or two;

or a pharmaceutically acceptable salt or prodrug thereof.

2. A compound according to claim 1 in which:
- R is optionally substituted phenyl or unsubstituted benzhydryl;
- R$^1$ is hydrogen or a group CH$_2$—Het where Het is as claimed in claim 1;
- R$^2$ is hydrogen, $C_{1-4}$alkyl or $C_{1-2}$alkoxy$C_{1-4}$alkyl;
- R$^3$ is hydrogen or $C_{1-6}$alkylcarbonyl;
- R$^4$ is methyl, trifluoromethyl, methoxy, ethoxy, isopropoxy or trifluoromethoxy; and
- R$^5$ is trifluoromethoxy or optionally substituted thiazole, 1,2,3-triazole, 1,2,4-triazole, or tetrazole.

3. A compound according to claim 1 in which R is phenyl, R$^1$, R$^2$ and R$^3$ are hydrogen, R$^4$ is methoxy, R$^5$ is

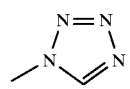

and R$^{6a}$ and R$^{6b}$ are hydrogen.

4. A compound according to claim 1 in which R is benzhydryl, R$^1$, R$^2$ and R$^3$ are hydrogen, R$^4$ is methoxy, R$^5$ is

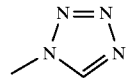

and R$^{6a}$ and R$^{6b}$ are hydrogen.

5. A process for preparing a compound according to claim 1 which comprises reacting a compound of formula (II):

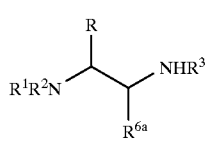

(II)

where R, R$^1$, R$^2$, and R$^3$ and R$^{6a}$ are as defined in claim 1 with the exception that R$^1$ may be a protecting group, with a compound of formula (III):

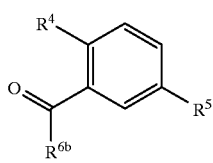

(III)

where R$^4$, R$^5$ and R$^{6b}$ are as defined in claim 1; or alternatively to prepare a compound according to claim 1 in which R$^1$ is not hydrogen reacting a compound of formula (IV):

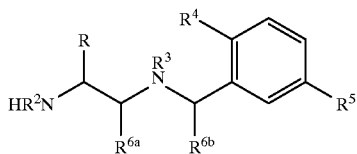

where R, $R^2$, $R^3$, $R^4$, $R^5$, $R^{6a}$ and $R^{6b}$ are as defined in claim 1 and $R^1$ is hydrogen, with a compound of formula (V):

LG—$R^{1a}$ where $R^{1a}$ is a group of the formula $(CH_2)_p$—Het as defined in claim 1 and LG is a leaving group;

or alternatively to prepare a compound according to claim 1 in which $R^5$ is a tetrazol-1-yl group and p is zero reacting a compound of formula (VI):

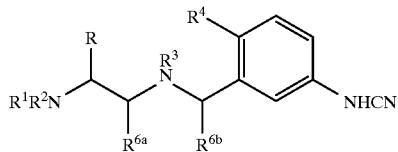

where R, $R^1$, $R^2$, $R^3$, $R^4$, $R^{6a}$ and $R^{6b}$ are as defined in claim 1, with ammonium chloride and sodium azide;

or alternatively to prepare a compound according to claim 1 reacting a compound of formula (VII) with a compound of formula (VIII):

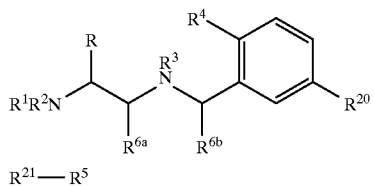

$R^{21}$—$R^5$ where R, $R^1$, $R^2$, $R^3$, $R^4$, $R^5$, $R^{6a}$ and $R^{6b}$ are as defined in claim 1 and one of $R^{20}$ and $R^{21}$ is $B(OH)_2$ or $Sn(alkyl)_3$ or a derivative thereof and the other is a leaving group;

each process being followed, where necessary, by the removal of any protecting group where present;

and when the compound of formula (I) is obtained as a mixture of enantiomers or diastereoisomers, optionally resolving the mixture to obtain the desired enantiomer; and/or, if desired, converting the resulting compound of formula (I) or a salt thereof, into a pharmaceutically acceptable salt thereof.

6. A pharmaceutical composition comprising a compound according to claim 1 and a pharmaceutically acceptable excipient.

7. A method of treatment of a subject suffering from a disorder associated with excess of tachykinin which comprises administering to that subject a therapeutically effective amount of a compound according to claim 1.

* * * * *